US00PP36507P2

(12) United States Plant Patent
van Dijk

(10) Patent No.: US PP36,507 P2
(45) Date of Patent: Feb. 25, 2025

(54) ***ANTHURIUM* PLANT NAMED 'AN2599066'**

(50) Latin Name: *Anthurium andreanum*
Varietal Denomination: AN2599066

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/607,511

(22) Filed: Mar. 17, 2024

(51) Int. Cl.
*A01H 5/02* (2018.01)
*A01H 6/10* (2018.01)

(52) U.S. Cl.
USPC ..... Plt./369

(58) Field of Classification Search
USPC ..... Plt./365, 369
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Anthurium* plant named 'AN2599066', characterized by its upright to outwardly arching and uniform plant habit; freely clumping growth habit; bushy and dense plants; narrowly cordate to narrowly deltoid dark green-colored leaves; freely flowering habit; inflorescences that are positioned within to slightly above the foliar plane on strong and erect scapes; broadly cordate red-colored spathes and white and yellow-colored spadices; and durable spathes that impart good inflorescence longevity.

2 Drawing Sheets

Figure 1:
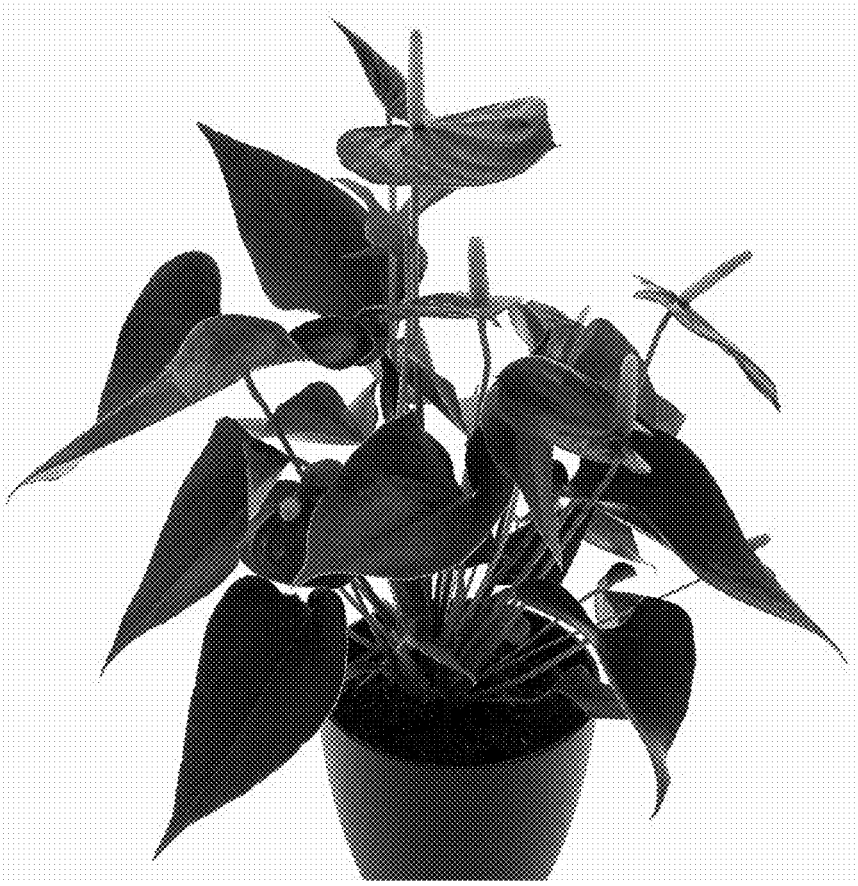

Botanical designation: *Anthurium andreanum.*
Cultivar denomination: 'AN2599066'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Nov. 22, 2022, application number 2022/2643. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Anthurium* plant, botanically known as *Anthurium andreanum* and hereinafter referred to by the name 'AN2599066'.

The new *Anthurium* plant is a product of a controlled breeding program conducted by the Inventor in Bleiswijk, The Netherlands. The objective of the breeding program is to create new freely-clumping *Anthurium* plants with durable and glossy spathes.

The new *Anthurium* plant originated from a cross-pollination made by the Inventor in January, 2013 in Bleiswijk, The Netherlands of a proprietary selection of *Anthurium*

*andreanum* identified as code number 07-017783-0003, not patented, as the female, or seed, parent with a proprietary selection of *Anthurium andreanum* identified as code number 06-015783-0005, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in December, 2014.

Asexual reproduction of the new *Anthurium* plant by in vitro meristem propagation in a controlled environment in Bleiswijk, The Netherlands since October, 2016 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2599066'. These characteristics in combination distinguish 'AN2599066' as a new and distinct *Anthurium* plant:

1. Upright to outwardly arching and uniform plant habit.
2. Freely clumping growth habit; bushy and dense plants.
3. Narrowly cordate to narrowly deltoid dark green-colored leaves.
4. Freely flowering habit.
5. Inflorescences that are positioned within to slightly above the foliar plane on strong and erect scapes.
6. Broadly cordate red-colored spathes and white and yellow-colored spadices.

7. Durable spathes that impart good inflorescence longevity.

Plants of the new *Anthurium* differ primarily from plants of the female parent selection in the following characteristics:

1. Plants of the new *Anthurium* are not as freely clumping as plants of the female parent selection.
2. Spathes of plants of the new *Anthurium* are smaller than spathes of plants of the female parent selection.
3. Spadices of plants of the new *Anthurium* are straighter than and not as curving as spadices of plants of the female parent selection.

Plants of the new *Anthurium* differ primarily from plants of the male parent selection in the following characteristics:

1. Plants of the new *Anthurium* are more compact than plants of the male parent selection.
2. Spathes of plants of the new *Anthurium* are flat to slightly convex whereas spathes of plants of the male parent selection are concave.
3. Spathes of plants of the new *Anthurium* are white and yellow in color whereas spathes of plants of the male parent selection are white and pink in color.

Plants of the new *Anthurium* can also be compared to plants of *Anthurium andreanum* 'Antherbi', disclosed in U.S. Plant Pat. No. 28,241. In side-by-side comparisons, plants of the new *Anthurium* differ primarily from plants of 'Antherbi' in the following characteristics:

1. Spathes of plants of the new *Anthurium* are larger than spathes of plants of 'Antherbi'.
2. Spathes of plants of the new *Anthurium* are not as rugose as spathes of plants of 'Antherbi'.
3. Spathes of plants of the new *Anthurium* are flat to slightly convex whereas spathes of plants of 'Antherbi' are concave.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2599066' grown in a container.

Figure 2:
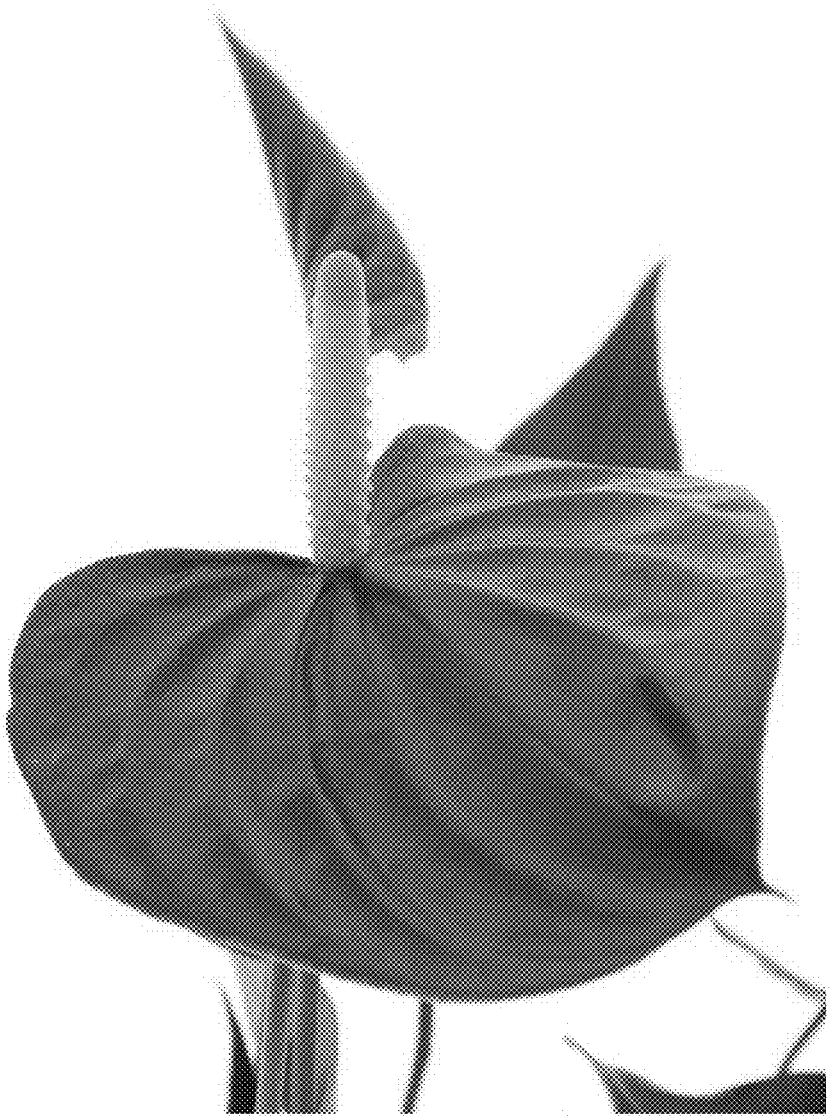

The photograph on the second sheet (FIG. 2) is a close-up view of typical inflorescences of 'AN2599066'.

DETAILED BOTANICAL DESCRIPTION

The aforementioned photographs and following observations and measurements describe plants grown in 12-cm containers in Bleiswijk, The Netherlands during the late autumn in a glass-covered greenhouse. Plants were grown under conditions and practices which approximate those generally used in commercial *Anthurium* production. During the production of the plants, day and night temperatures ranged from about 19° C. to 22.5° C. and light levels ranged from 100 μmol to 200 μmol. Plants were ten months old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2599066'.

Parentage:

*Female, or seed, parent*.—Proprietary selection of *Anthurium andreanum* identified as code number 07-017783-0003, not patented.

*Male, or pollen, parent*.—Proprietary selection of *Anthurium andreanum* identified as code number 06-015783-0005, not patented.

Propagation:

*Type*.—By in vitro meristem propagation.

*Time to initiate roots, summer and winter*.—About two weeks at temperatures about 19° C. to 22.5° C.

*Time to produce a rooted young plant, summer and winter*.—About six to eight weeks at temperatures about 19° C. to 22.5° C.

*Root description*.—Medium in thickness, fibrous; typically creamy white in color, actual color of the roots is dependent on substrate composition, water quality, fertilizer type and formulation, substrate temperature and physiological age of roots.

*Rooting habit*.—Freely branching, medium density.

Plant description:

*Plant shape*.—Upright to outwardly spreading and uniform plant habit; overall shape, broadly ovate to broadly elliptic.

*Growth habit*.—Freely clumping habit with about six clumps per plant imparting a bushy and dense appearance.

*Plant height, from soil level to top of leaf plane*.—About 24.6 cm.

*Plant height, from soil level to top of inflorescences*.—About 31 cm.

*Plant diameter or spread*.—About 35.6 cm.

Leaf description:

*Arrangement*.—Alternate; simple; about four leaves per clump.

*Length*.—About 16.7 cm.

*Width*.—About 10.1 cm.

*Shape*.—Narrowly cordate to narrowly deltoid.

*Apex*.—Apiculate with mucronate apex.

*Base*.—Shallowly cordate to hastate.

*Margin*.—Entire; moderate to strongly and coarsely undulate.

*Texture and luster, upper and lower surfaces*.—Smooth, glabrous; moderately leathery; glossy.

*Venation pattern*.—Pinnate.

*Color*.—Developing leaves, upper surface: Close to a blend of 144A and 146A. Developing leaves, lower surface: Close to 146B. Fully expanded leaves, upper surface: Close to NN137A; venation, close to 143C. Fully expanded leaves, lower surface: Close to a blend of 144A and 146B; venation, close to N144A.

*Petioles*.—Length: About 15.4 cm. Diameter: Distally, about 2.5 mm; proximally, about 3.5 mm. Strength: Strong. Texture and luster, upper and lower surfaces: Smooth, glabrous; slightly glossy. Color, upper surface: Close to a blend of 143A and 144A. Color, lower surface: Close to 144A. Geniculum length: About 1.8 cm. Geniculum diameter: About 3 mm. Geniculum texture and luster, upper and lower surfaces: Smooth, glabrous; slightly glossy. Geniculum color, upper surface: Close to 143A. Geniculum color, lower surface: Close to 144A. Wing length:

About 2 cm. Wing diameter: About 5 mm. Wing color: Close to 144B; towards the margins, close to 145B.

Inflorescence description:

*Inflorescence arrangement and flowering habit.*—Spathes with spadices held within and slightly above the foliar plane on strong and erect scapes; flowering structures arise from leaf axils; freely and continuous flowering year-round in controlled temperature greenhouses in The Netherlands; typically about nine developing and developed inflorescences per plant at one time; inflorescence development commences about 2.5 to 3.5 months after planting.

*Inflorescence longevity.*—Spathes maintain good substance for about two months on the plant; inflorescences persistent.

*Fragrance.*—None detected.

*Spathes.*—Length: About 8.7 cm. Width: About 8.6 cm. Shape: Broadly cordate; flat to slightly convex. Apex: Abruptly acute with a mucronate tip. Base: Cordate. Margin: Entire; slightly to moderately and coarsely undulate. Aspect: At about 90° from the peduncle axis. Texture and luster, upper and lower surfaces: Smooth, glabrous; moderately leathery; glossy. Color: When developing, front surface: Close to N45A; towards the base, close to 46A and at the base, tinged with close to 146D; narrow marginal edge, close to 185A; mucronate tip, close to 151D. When developing, rear surface: Close to 47A and 47B; towards the base, close to 48A and tinged with close to 146D; narrow marginal edge, close to 185A; mucronate tip, close to 151D. Fully developed, front surface: Close to N45B; towards the base, close to 46B, and at the base, tinged with close to 146A; narrow marginal edge, close to 46A; with subsequent development, color becoming closer to N45A and towards the base, tinged with close to 146D, with venation, close to 200B. Fully developed, rear surface: Close to 47B; towards the base, close to 47C and strongly tinged with close to 146D; narrow marginal edge, close to 185A; mucronate tip, close to 151B and 151C; with subsequent development, color becoming closer to 46B and towards the base, tinged with close to 146B, with venation, close to 200B.

*Spadices.*—Length: About 3.3 cm. Diameter: About 6 mm. Shape: Columnar, slightly tapering towards the apex; apex, obtuse; base, obtuse; in cross-section, rounded. Aspect: About 85° from the spathe axis and about 10° from the peduncle axis. Color: Immature: Close to 12B and distally, close to 154A. Mature: Close to 155D; with subsequent development, becoming closer to 153D. Flowers: Type: Hermaphroditic. Quantity per spadix: Numerous, about 160. Height: Less than 0.5 mm. Diameter: About 1.5 mm. Shape: Roughly square. Anther color: Close to 155D. Pollen amount: Scarce to moderate. Pollen color: Close to NN155A. Stigma color: Close to 155A.

*Scape.*—Length: About 22.7 cm. Diameter: About 3 mm. Strength: Strong. Aspect: About 15° from vertical. Color: Close to 144A.

*Seed and fruit.*—To date, seed and fruit development has not been observed on plants of the new *Anthurium.*

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures about 30° C. and to be hardy to USDA Hardiness Zone 10.

It is claimed:

1. A new and distinct *Anthurium* plant named 'AN2599066' as illustrated and described.

* * * * *